US006463361B1

(12) United States Patent
Wang et al.

(10) Patent No.: US 6,463,361 B1
(45) Date of Patent: Oct. 8, 2002

(54) SPEECH INTERFACE FOR AN AUTOMATED ENDOSCOPIC SYSTEM

(75) Inventors: Yulun Wang, Goleta, CA (US); Darrin Uecker, Santa Barbara, CA (US)

(73) Assignee: Computer Motion, Inc., Goleta, CA (US)

( * ) Notice: Subject to any disclaimer, the term of this patent is extended or adjusted under 35 U.S.C. 154(b) by 0 days.

(21) Appl. No.: 08/310,665

(22) Filed: Sep. 22, 1994

(51) Int. Cl.$^7$ .......................... G05B 15/00; G06F 19/00
(52) U.S. Cl. ...................... 700/258; 700/245
(58) Field of Search .......................... 395/99, 92, 93, 395/2.84; 364/413.13, 413.02; 128/4, 20, 897, 782; 700/258, 245

(56) References Cited

U.S. PATENT DOCUMENTS

| | | |
|---|---|---|
| 977,825 A | 12/1910 | Murphy |
| 3,171,549 A | 3/1965 | Orloff |
| 3,280,991 A | 10/1966 | Melton et al. |
| 4,058,001 A | 11/1977 | Waxman |
| 4,128,880 A | 12/1978 | Cray, Jr. |
| 4,221,997 A | 9/1980 | Flemming ................. 395/80 |
| 4,367,998 A | 1/1983 | Causer |
| 4,401,852 A | 8/1983 | Noso et al. |
| 4,456,961 A | 6/1984 | Price et al. ................ 364/191 |
| 4,460,302 A | 7/1984 | Moreau et al. |
| 4,474,174 A | 10/1984 | Petruzzi ................... 128/4 |
| 4,491,135 A | 1/1985 | Klein |
| 4,503,854 A | 3/1985 | Jako |
| 4,517,963 A | 5/1985 | Michel ..................... 128/6 |
| 4,523,884 A | 6/1985 | Clement et al. |
| 4,586,398 A | 5/1986 | Yindra |
| 4,604,016 A | 8/1986 | Joyce |
| 4,616,637 A | 10/1986 | Caspari et al. |
| 4,624,011 A | 11/1986 | Watanabe et al. |
| 4,633,389 A | 12/1986 | Tanaka et al. |
| 4,635,292 A | 1/1987 | Mori et al. |

(List continued on next page.)

FOREIGN PATENT DOCUMENTS

| DE | 9204118 U | 7/1992 |
|---|---|---|
| DE | 4310842 C2 | 1/1995 |

(List continued on next page.)

OTHER PUBLICATIONS

"Endocorporeal Surgery Using Remote Manipulators" (Ned. S. Rasor and J.W. Spickler) Remotely Manned Systems—Exploration and Operation in Space, California Institute of Technology 1973.

"A Survey Study of Teleoperators, Robotics, and Remote Systems Technology" (Arthur D. Alexander, III) Remotely Manned Systems—Exploration and Operation in Space, California Institute of Technology 1973.

"Impacts of Telemation on Modern Society" (Arthur D. Alexander, III), On the Theory and Practice of Robots and Manipulators vol. II, 1974.

Transcript of a video presented by SRI at the 3rd World Congress of Endoscopic Surgery in Bordeaux on Jun. 18–20, 1992, in Washington on Apr. 9, 1992, and in San Diego, CA on Jun. 4–7, 1992 entitled "Telepresence Surgery—The Future of Minimally Invasive Medicine".

(List continued on next page.)

*Primary Examiner*—George B. Davis
(74) *Attorney, Agent, or Firm*—Irell & Manella, LLP (57) ABSTRACT

A robotic system which controls the movement of a surgical instrument in response to voice commands from the user. The robotic system has a computer controlled arm that holds the surgical instrument. The user provides voice commands to the computer through a microphone. The computer contains a phrase recognizer that matches the user' speech with words stored in the computer. Matched words are then processed to determine whether the user has spoken a robot command. If the user has spoken a recognized robot command the computer will move the robotic arm in accordance with the command.

26 Claims, 3 Drawing Sheets

U.S. PATENT DOCUMENTS

| | | | |
|---|---|---|---|
| 4,641,292 A | 2/1987 | Tunnell et al. | |
| 4,655,257 A | 4/1987 | Iwashita | 128/4 |
| 4,672,963 A | 6/1987 | Barken | |
| 4,676,243 A | 6/1987 | Clayman | 128/305 |
| 4,728,974 A | 3/1988 | Nio et al. | 354/81 |
| 4,762,455 A | 8/1988 | Coughlan et al. | |
| 4,791,934 A | 12/1988 | Brunnett | 128/653 |
| 4,791,940 A | 12/1988 | Hirschfeld et al. | |
| 4,794,912 A | 1/1989 | Lia | 128/4 |
| 4,815,006 A | 3/1989 | Anderson et al. | 395/86 |
| 4,815,450 A | 3/1989 | Patel | |
| 4,837,734 A | 6/1989 | Ichikawa et al. | |
| 4,852,083 A | 7/1989 | Niehaus et al. | |
| 4,853,874 A | 8/1989 | Iwamoto et al. | |
| 4,854,301 A | 8/1989 | Nakajima | 128/4 |
| 4,860,215 A | 8/1989 | Seraji | |
| 4,863,133 A | 9/1989 | Bonnell | |
| 4,883,400 A | 11/1989 | Kuban et al. | |
| 4,930,494 A | 6/1990 | Takehana et al. | 128/4 |
| 4,945,479 A | 7/1990 | Rusterholz et al. | |
| 4,949,717 A | 8/1990 | Shaw | |
| 4,954,952 A | 9/1990 | Ubhayakar et al. | |
| 4,965,417 A | 10/1990 | Massie | |
| 4,969,709 A | 11/1990 | Sogawa et al. | |
| 4,969,890 A | 11/1990 | Sugita et al. | |
| 4,979,933 A | 12/1990 | Runge | 493/215 |
| 4,979,949 A | 12/1990 | Matsen, III et al. | 395/80 |
| 4,980,626 A | 12/1990 | Hess et al. | |
| 4,989,253 A | 1/1991 | Liang et al. | 381/110 |
| 4,996,975 A | 3/1991 | Nakamura | 128/6 |
| 5,019,968 A | 5/1991 | Wang et al. | |
| 5,020,001 A | 5/1991 | Yamamoto et al. | 395/86 |
| 5,065,741 A | 11/1991 | Uchlyama et al. | 128/660.03 |
| 5,078,140 A | 1/1992 | Kwoh | 901/6 |
| 5,086,401 A | 2/1992 | Glassman et al. | 395/89 |
| 5,091,656 A | 2/1992 | Gahn | |
| 5,097,829 A | 3/1992 | Quisenberry | |
| 5,097,839 A | 3/1992 | Allen | |
| 5,098,426 A | 3/1992 | Sklar et al. | |
| 5,105,367 A | 4/1992 | Tsuchihashi et al. | |
| 5,109,499 A | 4/1992 | Inagami et al. | |
| 5,123,095 A | 6/1992 | Papadopulos et al. | |
| 5,131,105 A | 7/1992 | Harrawood et al. | |
| 5,142,930 A | 9/1992 | Allen et al. | 901/47 |
| 5,145,227 A | 9/1992 | Monford, Jr. | 244/161 |
| 5,166,513 A | 11/1992 | Keenan et al. | |
| 5,175,694 A | 12/1992 | Amato | 364/516 |
| 5,182,641 A | 1/1993 | Diner et al. | |
| 5,184,601 A | 2/1993 | Putman | 128/6 |
| 5,187,574 A | 2/1993 | Kosemura et al. | 358/108 |
| 5,196,688 A | 3/1993 | Hesse et al. | 382/42 |
| 5,201,325 A * | 4/1993 | McEwen et al. | 128/20 |
| 5,201,743 A | 4/1993 | Haber et al. | |
| 5,217,003 A | 6/1993 | Wilk | 128/4 |
| 5,221,283 A | 6/1993 | Chang | |
| 5,228,429 A | 7/1993 | Hatano | 128/4 |
| 5,230,623 A * | 7/1993 | Guthrie et al. | 433/72 |
| 5,236,432 A | 8/1993 | Matsen, III et al. | |
| 5,251,127 A | 10/1993 | Raab | 364/413.13 |
| 5,257,999 A | 11/1993 | Slanetz, Jr. | |
| 5,271,384 A | 12/1993 | McEwen et al. | 128/26 |
| 5,279,309 A | 1/1994 | Taylor et al. | 128/782 |
| 5,282,806 A | 2/1994 | Haber | |
| 5,289,273 A * | 2/1994 | Lang | 348/121 |
| 5,289,365 A | 2/1994 | Caldwell et al. | |
| 5,299,288 A | 3/1994 | Glassman et al. | |
| 5,300,926 A * | 4/1994 | Stoecki | 364/413.01 |
| 5,303,148 A | 4/1994 | Mattson et al. | |
| 5,304,185 A | 4/1994 | Taylor | |
| 5,305,203 A | 4/1994 | Raab | 364/413.13 |
| 5,305,427 A | 4/1994 | Nagata | 395/94 |
| 5,309,717 A | 5/1994 | Minch | |
| 5,313,306 A | 5/1994 | Kuban et al. | 348/65 |
| 5,320,630 A * | 6/1994 | Ahmed | 606/140 |
| 5,337,732 A | 8/1994 | Grundfest et al. | |
| 5,339,799 A | 8/1994 | Kami et al. | |
| 5,343,385 A | 8/1994 | Joskowicz et al. | |
| 5,343,391 A * | 8/1994 | Musbabac | 364/413.28 |
| 5,345,538 A | 9/1994 | Narayannan et al. | 395/2.84 |
| 5,357,962 A | 10/1994 | Green | |
| 5,368,015 A | 11/1994 | Wilk | |
| 5,368,428 A | 11/1994 | Hussey et al. | 901/47 |
| 5,371,536 A | 12/1994 | Yamaguchi | 348/169 |
| 5,382,885 A | 1/1995 | Salcudean et al. | |
| 5,388,987 A * | 2/1995 | Badoz et al. | 606/18 |
| 5,395,369 A | 3/1995 | McBrayer et al. | |
| 5,397,323 A | 3/1995 | Taylor et al. | |
| 5,402,801 A * | 4/1995 | Talyor | 128/898 |
| 5,403,319 A * | 4/1995 | Matsen, III et al. | 606/88 |
| 5,408,409 A | 4/1995 | Glassman et al. | |
| 5,410,638 A | 4/1995 | Colgate et al. | 395/99 |
| 5,417,210 A | 5/1995 | Funda et al. | 128/4 |
| 5,417,701 A | 5/1995 | Holmes | |
| 5,422,521 A | 6/1995 | Neer et al. | |
| 5,431,645 A | 7/1995 | Smith et al. | 606/1 |
| 5,434,457 A * | 7/1995 | Josephs et al. | 307/326 |
| 5,442,728 A | 8/1995 | Kaufman et al. | |
| 5,443,484 A | 8/1995 | Kirsch et al. | |
| 5,445,166 A | 8/1995 | Taylor | |
| 5,451,924 A | 9/1995 | Massimino et al. | 340/407.1 |
| 5,455,766 A | 10/1995 | Scheller et al. | |
| 5,458,547 A | 10/1995 | Teraoka et al. | |
| 5,458,574 A | 10/1995 | Machold et al. | |
| 5,476,010 A | 12/1995 | Fleming et al. | |
| 5,490,117 A | 2/1996 | Oda et al. | |
| 5,490,843 A | 2/1996 | Hildwein et al. | |
| 5,506,912 A | 4/1996 | Nagasaki et al. | |
| 5,512,919 A | 4/1996 | Araki | |
| 5,515,478 A | 5/1996 | Wang | |
| 5,553,198 A | 9/1996 | Wang et al. | |
| 5,571,110 A | 11/1996 | Matsen, III et al. | |
| 5,572,999 A | 11/1996 | Funda et al. | |
| 5,609,560 A | 3/1997 | Ichikawa et al. | |
| 5,626,595 A | 5/1997 | Sklar et al. | |
| 5,629,594 A | 5/1997 | Jacobus et al. | |
| 5,630,431 A | 5/1997 | Taylor | |
| 5,631,973 A | 5/1997 | Green | |
| 5,657,429 A | 8/1997 | Wang et al. | |
| 5,658,250 A | 8/1997 | Blomquist et al. | |
| 5,676,673 A | 10/1997 | Ferre et al. | |
| 5,695,500 A | 12/1997 | Taylor et al. | |
| 5,696,837 A | 12/1997 | Green | |
| 5,735,290 A | 4/1998 | Sterman et al. | |
| 5,749,362 A | 5/1998 | Funda et al. | |
| 5,754,741 A | 5/1998 | Wang et al. | |
| 5,776,126 A | 7/1998 | Wilk et al. | |
| 5,779,623 A | 7/1998 | Bonnell | |
| 5,800,423 A | 9/1998 | Jensen | |
| 5,807,284 A | 9/1998 | Foxlin | |
| 5,808,665 A | 9/1998 | Green | |
| 5,813,813 A | 9/1998 | Daum et al. | |
| 5,817,084 A | 10/1998 | Jensen | |
| 5,859,934 A | 1/1999 | Green | |
| 5,878,193 A | 3/1999 | Wang et al. | |
| 5,931,832 A | 8/1999 | Jensen | |
| 5,950,629 A | 9/1999 | Taylor et al. | |
| 6,024,695 A | 2/2000 | Taylor et al. | |

FOREIGN PATENT DOCUMENTS

| | | |
|---|---|---|
| EP | 0239409 | 9/1987 |
| EP | 0424687 A1 | 5/1991 |

| | | |
|---|---|---|
| EP | 0776738 A2 | 6/1997 |
| WO | WO 91/04711 | 4/1991 |
| WO | WO 92/20295 | 11/1992 |
| WO | WO 93/13916 | 7/1993 |
| WO | WO 94/18881 | 9/1994 |
| WO | WO 94/26167 | 11/1994 |
| WO | WO 97/15240 | 5/1997 |
| WO | WO 98/25666 | 6/1998 |

OTHER PUBLICATIONS

Statutory Declaration of Dr. Philip S. Green, presenter of the video entitled "Telepresence Surgery—The Future of Minimally Invasive Medicine".

Abstract of a presentation "Telepresence: Advanced Teleoperator Technology for Minimally Invasive Surgery" (P. Green et al.) given at the 3rd World Congress of Endoscopic Surgery in Bordeaux, Jun. 18–20, 1992.

Abstract of a presentation "Telepresence: Advanced Teleoperator Technology for Minimally Invasive Surgery" (P. Green et al.) given at "Medicine meets virtual reality", symposium in San Diego, Jun. 4–7, 1992.

Abstract of a presentation "Camera Control for Laparoscopic Surgery by Speech–Recognizing Robot: Constant Attention and Better Use of Personnel" (Colin Besant et al.) given at the 3rd World Congress of Endoscopic Surgery in Bordeaux, Jun. 18–20, 1992.

"A Literature Review: Robots in Medicine" (B. Preising et al.) IEEE Jun. 1991.

"Robots for the Operating Room" (Elizabeth Corcoran), The New York Times, Sunday Jul. 19, 1992, Section 3, p. 9, col. 1.

"Taming the Bull: Safety in a Precise Surgical Robot" (Russell H. Taylor et al.), IEEE 1991.

Abstract of a presentation "Design Considerations of a New Generation Endoscope Using Robotics and Computer Vision Technology" (S.M. Krishnan et al.) given at the 3rd World Congress of Endoscopic Surgery in Bordeaux, Jun. 18–20, 1992.

Abstract of a presentation "3–D Vision Technology Applied to Advanced Minimally Invasive Surgery Systems" given at the 3rd World Congress of Endoscopic Surgery in Bordeaux, Jun. 18–20, 1992.

"Analysis of the Surgeon's Grasp for Telerobotic Surgical Manipulation" (Frank Tendick and Lawrence Stark), IEEE 1989.

"Kinematic Control and Visual Display of Redundant Teleoperators" (Hardi Das et al.), IEEE 1989.

"A New System for Computer Assisted Neurosurgery" (S. Lavallee), IEEE 1989.

"An Advanced Control Micromanipulator for Surgical Applications" (Ben Gayed et al.), Systems Science vol. 13 1987.

"Force Feedback–Based Telemicromanipulation for Robot Surgery on Soft Tissues" (A.M. Sabatini et al.), IEEE 1989.

"Six–Axis Bilateral Control of an Articulated Slave Manipulator Using a Cartesian Master Manipulator" (Masao Inoue), Advanced Robotics 1990.

"On a Micro–Manipulator for Medical Application—Stability Consideration of its Bilateral Controller" (S. Majima et al.), Mechatronics 1991.

"Anthropomorphic Remote Manipulator", NASA Tech Briefs 1991.

"Controlling Remote Manipulators through Kinesthetic Coupling" (A.K. Bejczy), Computers in Mechanical Engineering 1983.

"Design of a Surgeon–Machine Interface for Teleoperated Microsurgery" (Steve Charles M.D. et al.), IEEE 1989.

"A Robot in an Operating Room: A Bull in a China Shop" (J.M. Dolan et al.), IEEE 1987.

Abstract of a presentation "Concept and Experimental Application of a Surgical Robotic System the Steerable MIS Instrument SMI" given at the 3rd World Congress of Endoscopic Surgery in Bordeaux, Jun. 18–20, 1992.

Abstract of a presentation given at the 3rd World Congress of Endoscopic Surgery in Bordeaux, Jun. 18–20, 1992, entitled "Session 15/1".

Abstract of a presentation "A Pneumatic Controlled Sewing Device for Endoscopic Application the MIS Sewing Instrument MSI" given at the 3rd World Congress of Endoscopic Surgery in Bordeaux, Jun. 18–20, 1992.

Abstract of a presentation given at the 3rd World Congress of Endoscopic Surgery in Bordeaux (Jun. 18 to 20, 1992), entitled "Session 15/2".

Abstract of a presentation given at the 3rd World Congress of Endoscopic Surgery in Bordeaux (Jun. 18 to 20, 1992), entitled Session 15/4.

Abstract of a presentation given at the 3rd World Congress of Endoscopic Surgery in Bordeaux (Jun. 18 to 20, 1992), entitled "Session 15/5".

"Properties of Master–Slave Robots" (C. Vibet), Motor–con 1987.

"A New Microsurgical Robot System for Corneal Transplantation" (Noriyuki Tejima), Precision Machinery 1988.

"Human/Robot Interaction via the Transfer of Power and Information Signals—Part I: Dynamics and Control Analysis" (H. Kazerooni), IEEE 1989.

"Human/Robot Interaction via the Transfer of Power and Information Signals—Part II: An Experimental Analysis" (H. Kazerooni), IEEE 1989.

"Power and Impedance Scaling in Bilateral Manipulation" (J. Edward Colgate), IEEE 1991.

"S.M.O.S.: Stereotaxical Microtelemanipulator for Ocular Surgery" (Aicha Guerrouad and Pierre Vidal), IEEE 1989.

"Motion Control for a Sheep Shearing Robot" (James P. Trevelyan et al.), Proceedings of the 1st International Symposium on Robotics Research, MIT, Cambridge, Massachusetts, USA, 1983.

"Robots and Telechirs" (M.W. Thring), Wiley 1983.

Industrial Robotics (Gordon M. Mair), Prentice Hall 1988 (pp. 41–43, 49–50, 54, 203–209 enclosed).

"Student Reference Manual for Electronic Instrumentation Laboratories" (Wolf et al.), Prentice Hall, New Jersey 1990, pp. 498 and 499.

Fu, et al, "Robotics: Control, Sensing, Vision and Intelligence", McGraw–Hill Book Company; 1987.

* cited by examiner

SPEECH INTERFACE FOR AN AUTOMATED ENDOSCOPIC SYSTEM

BACKGROUND OF THE INVENTION

1. Field of the Invention

The present invention relates to a robotic system that moves a surgical instrument in response to voice commands from the user.

2. Description of Related Art

To reduce the invasiveness of surgery, endoscopes are commonly utilized to view the internal organs of a patient. One end of the endoscope contains a lens which is inserted into the patient through a small incision in the skin. The lens focuses an image that is transmitted by fiber optic cable to a camera located at the opposite end of the endoscope. The camera is coupled to a monitor that displays the image of the patient.

The endoscope can be used in conjunction with another surgical instrument that is inserted into the patient. An assistant typically hold the endoscope while the surgeon manipulates the surgical instrument. The assistant moves the endoscope in response to instructions from the surgeon. Any miscommunication between the surgeon and the assistant may result in an error in the movement of the endoscope, thereby requiring the surgeon to repeat the instruction. Additionally, holding the endoscope for a significant amount of time may cause the assistant to become fatigued.

U.S. application Ser. No. 07/927,801 discloses a robotic arm that holds and moves an endoscope. The surgeon can move the robotic arm by depressing a foot pedal. The foot pedal is connected to a computer which moves the arm and the scope. Although the '801 system effectively moves the endoscope, the surgeon must continually manipulate the foot pedal, a process which may detract from the surgical procedure. It would be desirable to provide a robotic endoscopic system that can be controlled by voice commands from the user.

SUMMARY OF THE INVENTION

The present invention is a robotic system which controls the movement of a surgical instrument in response to voice commands from the user. The robotic system has a computer controlled arm that holds the surgical instrument. The user provides voice commands to the computer through a microphone. The computer contains a phrase recognizer that matches the user's speech with words stored in the computer. Matched words are then processed to determine whether the user has spoken a robot command. If the user has spoken a recognized robot command the computer will move the robotic arm in accordance with the command.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
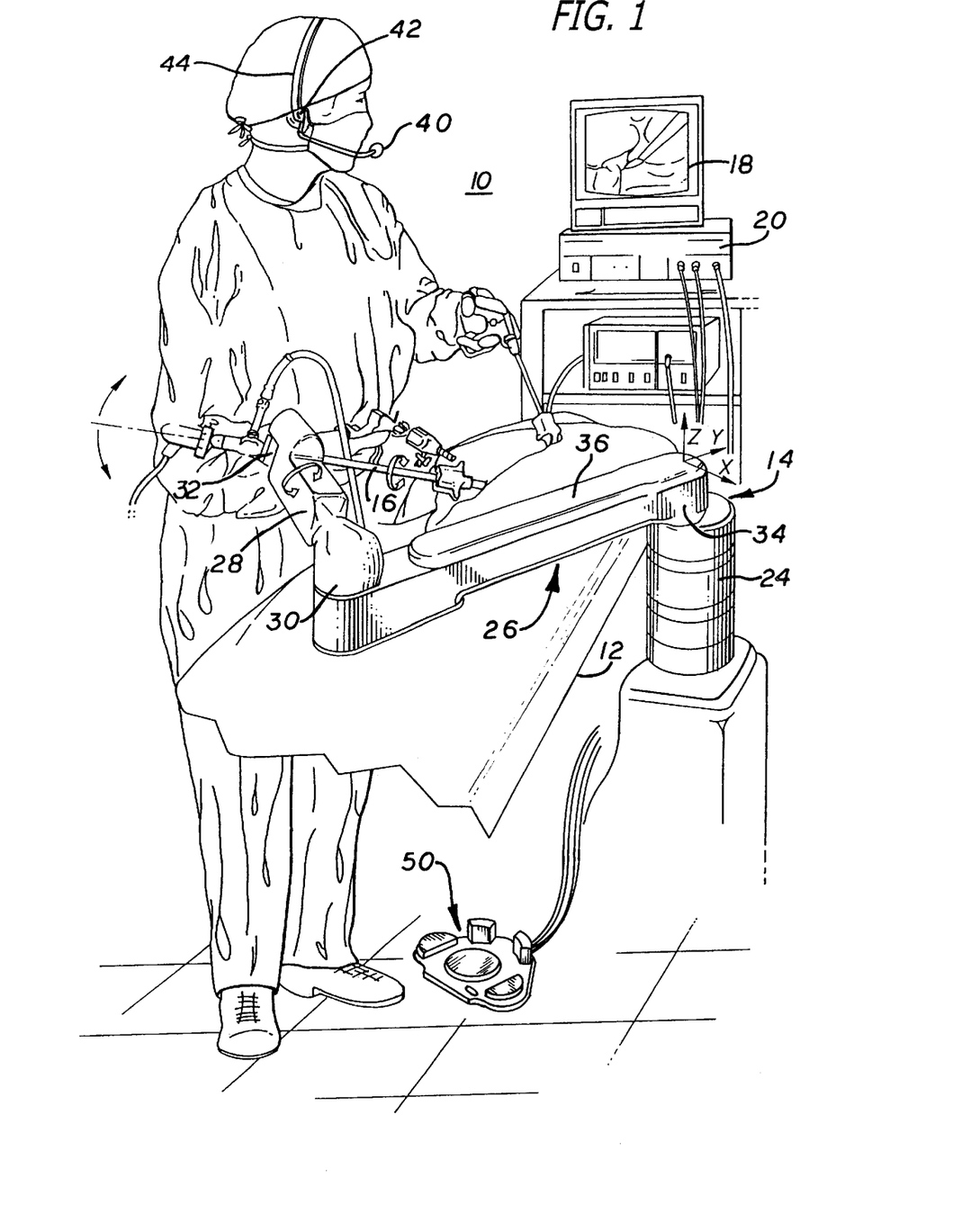
FIG. 1 is a perspective view of a robotic endoscope system of the present invention.

Referring to the drawings more particularly by reference numbers, FIG. 1 shows a robotic system 10 of the present invention. The system 10 is typically used in a sterile operating room where a surgeon performs a surgical procedure on a patient. The patient is placed on a operating table 12. Attached to the table 12 is a robotic arm assembly 14 which can move a surgical instrument 16 relative to the table 12 and the patient. The surgical instrument 16 is typically an endoscope which is inserted into the abdomen of the patient 12. The endoscope 16 enters the patient through a cannula, wherein the scope 16 rotate about a cannula pivot point. The endoscope is typically connected to a monitor 18 which allows the surgeon to view the organs, etc. of the patient. Although an endoscope is described and shown, it is to be understood that the present invention can be used with other surgical instruments.

The robotic arm assembly 14 controlled by a computer 20. In the preferred embodiment, the robotic arm assembly 16 includes a linear actuator 24 fixed to the table 14. The linear actuator 24 is connected to a linkage arm assembly 26 and adapted to move the linkage assembly 26 along the z axis of a first coordinate system. The first coordinate system also has an x axis and a y axis.

Figure 2:
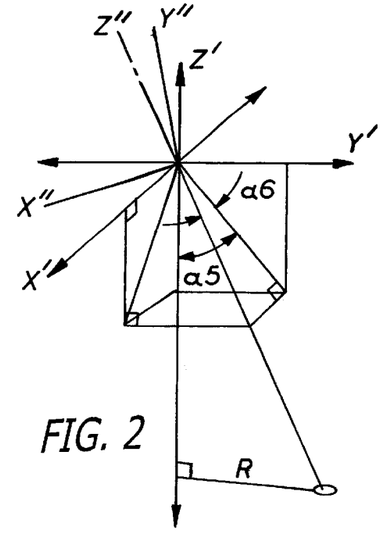
FIG. 2 is a schematic of an endoscope within two separate coordinate systems.

The linkage arm assembly 26 includes a first linkage arm 28 attached to a first rotary actuator 30 and an end effector 32. The first rotary actuator 30 is adapted to rotate the first linkage arm 28 and end effector 32 in a plane perpendicular to the z axis (x-y plane). The first rotary actuator 30 is connected to a second rotary actuator 34 by a second linkage arm 36. The second actuator 34 is adapted to rotate the first actuator 30 in the x-y plane. The second rotary actuator 34 is connected to the output shaft of the linear actuator 24. The actuators 24, 30 and 34 rotate in response to output signals provided by the computer 20. As shown in FIG. 2, the junction of the endoscope 16 and the end effector 32 define a second coordinate system which has an x' axis, a y' axis and a z' axis. The junction of the end effector 32 and endoscope 18 also define the origin of a third coordinate system which has a x" axis, a y" axis and a z" axis. The z" axis parallel with the longitudinal axis of the endoscope 16.

The arm assembly may have a pair of passive joints that allow the end effector to be rotated in the direction indicated by the arrows. The actuators 24, 30 and 34, and joints of the arm may each have position sensors (not shown) that are connected to the computer 20. The sensors provide positional feedback signals of each corresponding arm component.

The system has a microphone 40 that is connected to the computer 20. The system may also have a speaker 42 that is connected to the computer 20. The microphone 40 and speaker 42 may be mounted to a headset 44 that is worn by the user. Placing the microphone 40 in close proximity to the user reduces the amount of background noise provided to the computer and decreases the probability of an inadvertent input command.

Figure 3:
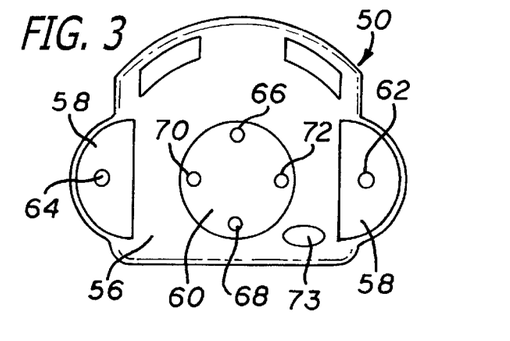
FIG. 3 is a top view of a foot pedal.

As shown in FIG. 3, the system may also have a foot pedal 50. The foot pedal 22 has a housing 56 that supports a pair of outer first foot switches 58 and a second foot switch 60. One outer foot switch 58 has a first pressure transducer 62 and the other switch has a second pressure transducer 64. The second foot switch 60 has third 66, fourth 68, fifth 70 and sixth 72 pressure transducers. The transducers are each connected to a corresponding operational amplifier that provides a voltage input to the computer 20. The pressure transducers 62–72 are preferably constructed so that the resistance of each transducer decreases as the surgeon increases the pressure on the foot switches. Such a transducer is sold by Interlink Electronics. The decreasing transducer resistance increases the input voltage provided to the computer 20 from the operational amplifier. Each transducer corresponds to a predetermined direction within the image displayed by the monitor. In the preferred embodiment, the first pressure transducer 62 corresponds to moving the endoscope toward the image viewed by the surgeon. The second transducer 64 moves the scope away from the image. The third 66 and fourth 68 transducers move the image "up" and "down", respectively, and the fifth 70 and sixth 72 transducers move the image "left" and "right", respectively. The pedal may have a button 73 that enables the foot pedal 50 and disable the voice command feature, or vice versa.

Figure 4:
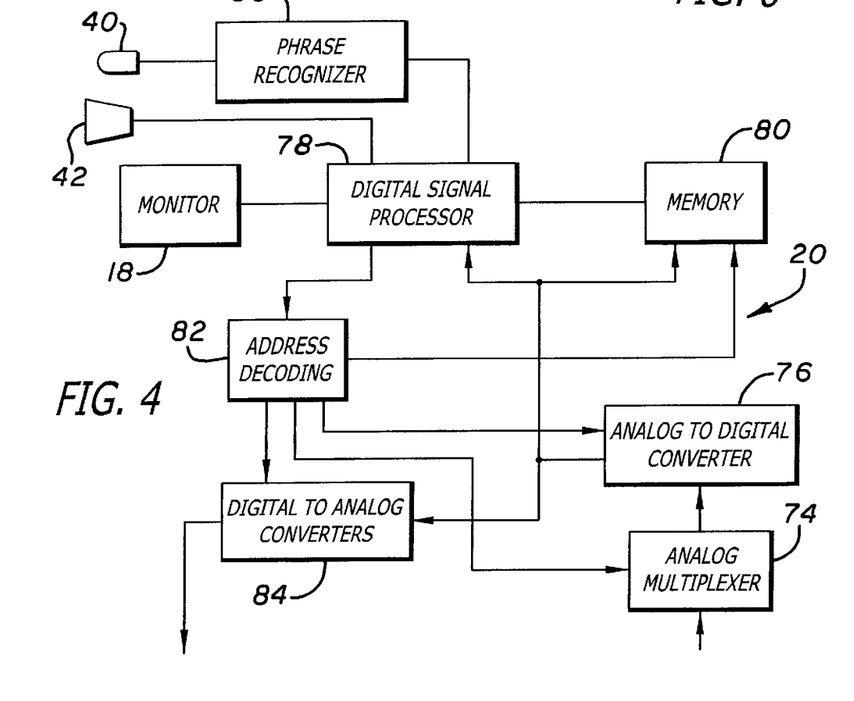
FIG. 4 is a schematic of a computer system.

FIG. 4 shows a schematic of the computer 20. The computer 20 has a multiplexer 74 which is connected to the pressure transducers of the foot pedal 50 and the position sensors of the arm. The multiplexer 74 is connected to a single analog to digital (A/D) converter 76. The computer 20 also has a processor 78 and memory 80.

The processor 78 is connected to an address decoder 82 and separate digital to analog (D/A) converters 84. Each D/A converter is connected to an actuator 24, 30 and 34. The D/A converters 84 provide analog output signals to the actuators in response to output signals received from the processor 78. The analog output signals have a sufficient voltage level to energize the electric motors and move the robotic arm assembly. The decoder 82 correlates the addresses provided by the processor with a corresponding D/A converter, so that the correct motor(s) is driven. The address decoder 82 also provides an address for the input data from the A/D converter 76 so that the data is associated with the correct input channel.

The computer 20 has a phrase recognizer 86 connected to the microphone 40 and the processor 78. The phrase recognizer 86 digitizes voice commands provided by the user through the microphone 40. The voice commands are then processed to convert the spoken words into electronic form. The electronic words are typically generated by matching the user's speech with words stored within the computer 20. In the preferred embodiment, the recognizer 86 is an electronic board with accompanying software that is marketed by Scott Instruments of Denton, Texas under the trademark "Coretechs Technology".

The electronic words are provided to the processor 78. The processor 78 compares a word, or a combination of words to predefined robot commands that are stored within a library in the memory 80 of the computer 20. If a word, or combination of words match a word or combination of words in the library, the processor 78 provides output commands to the D/A converter 84 to move the robotic arm in accordance with the command.

Figure 5:
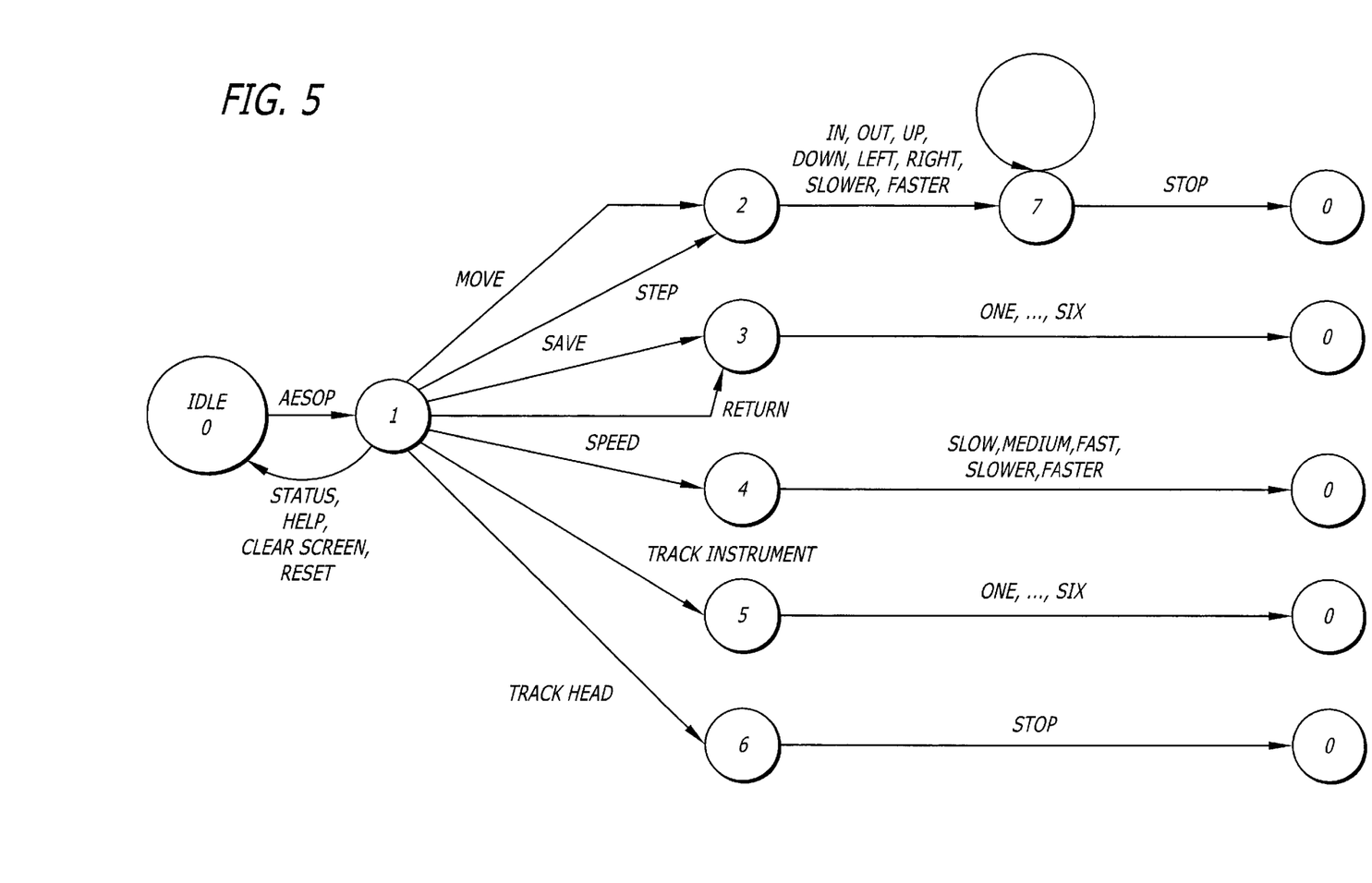
FIG. 5 is a schematic of a grammar process.

FIG. 5 shows exemplary words and combinations of words that provide robot commands. A grammar process is performed to determine whether the voice commands satisfy certain conditions. The process contains a number of states advanced by the satisfaction of a condition. If the voice command provided by the user satisfies a first condition, then the process proceeds to the first state. If a condition of a next state is satisfied then the process proceeds to the next corresponding state, and so forth and so on. For example, to prevent a robot command from being inadvertently spoken, it is desirable to predicate all voice commands with a qualifier. For example, the qualifier may be a name given to the robot such as "AESOP". Therefore when the user provides a voice command, the process initially determines whether the spoken word is AESOP. If the spoken word is not AESOP then the process ends. The term "stop" may be an exception to this rule, wherein the computer will stop arm movement when the user provides a simple "stop" voice command.

If the spoken word is AESOP the process continues to state 1. The process next determines whether the user has spoken a word that satisfies a condition to advance to states 2–6. These words include "move", "step", "save", "return", "speed", "track instrument" and "track head". The track instrument command is for a system which has the ability to move an endoscope to automatically track the movement of a second instrument that is inserted into the patient. The track head command may enable the system so that the endoscope movement tracks the user's eyes. For example, if the user looks to the right of the image displayed by the monitor, the robot will move the endoscope to move the image in a rightward direction. The move and step commands induce movement of the scope in a desired direction. The save command saves the position of the endoscope within the memory of the computer. The return command will return the scope to a saved position.

From states 2–6 the process will determine whether the user has spoken words that meet the next condition and so forth and so on. When a certain number of conditions have been met, the processor 78 will provide an output command to the D/A converter 84 in accordance with the voice commands. For example, if the user says "AESOP move left", the processor 78 will provide output commands to move the endoscope 12, so that the image displayed by the monitor moves in a leftward direction. The microphone 40 phrase recognizer 86 and grammar process essentially provide the same input function as the foot pedal 50, multiplexer 74 and A/D converter 76.

The processor 78 can also provide the user with feedback regarding the recognized command through the speaker 42 or the monitor 18. For example, when the user states "AESOP move right", after processing the speech, the processor 78 can provide an audio message through the speaker 42, or a visual message on the monitor 18, "AESOP move right". Additionally, the processor 78 can provide messages regarding system errors, or the present state of the system such as "speed is set for slow".

Figure 6:
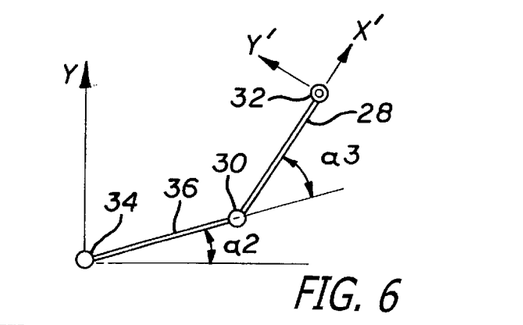
FIG. 6 is a schematic of a robotic arm.

Referring to FIG. 6, the processor 78 typically computes the movement of the robotic arm assembly 16 in accordance with the following equations.

$$a3 = \pi - \cos^{-1}\left(\frac{x^2 + y^2 - L1^2 + L2^2}{-2L1L2}\right) \quad (1)$$

$$\Delta = \cos^{-1}\left(\frac{x^2 + y^2 + L1^2 - L2^2}{2 \cdot L1\sqrt{x^2 + y^2}}\right)$$

$$a0 = \tan^{-1} 2\left(\frac{y}{x}\right)$$

$$a2 = a0 + l - \Delta$$

where;
- a2=angle between the second linkage arm 36 and the x axis.
- a3=angle between the first linkage arm 28 and the longitudinal axis of the second linkage arm 36.
- L1=length of the second linkage arm.
- L2=length of the first linkage arm.

x=x coordinate of the end effector in the first coordinate system.

y=y coordinate of the end effector in the first coordinate system.

To move the end effector to a new location of the x-y plane the processor 78 computes the change in angles a2 and a3 and then provides output signals to move the actuators accordingly. The original angular position of the end effector is provided to the processor 78 by the position sensors. The processor moves the linkage arms an angle that corresponds to the difference between the new location and the original location of the end effector. A differential angle Δa2 corresponds to the amount of angular displacement provided by the second actuator 34, a differential angle Δa3 corresponds to the amount of angular displacement provided by the first actuator 30.

To improve the effectiveness of the system 10, the system is constructed so that the desired movement of the surgical instrument correlates to a direction relative to the image displayed by the monitor. Thus when the surgeon commands the scope to move up, the scope always appears to move in the up direction. To accomplish this result, the processor 78 converts the desired movement of the end of the endoscope in the third coordinate system to coordinates in the second coordinate system, and then converts the coordinates of the second coordinate system into the coordinates of the first coordinate system.

Referring to FIG. 2, the desired movement of the endoscope is converted from the third coordinate system to the second coordinate system by using the following transformation matrix;

$$\begin{pmatrix} \Delta x' \\ \Delta y' \\ \Delta z' \end{pmatrix} = \begin{pmatrix} \cos(a6) & 0 & -\sin(a6) \\ -\sin(a5)\sin(a6) & \cos(a5) & -\sin(a5)\cos(a6) \\ \cos(a5)\sin(a6) & \sin(a5) & \cos(a5)\cos(a6) \end{pmatrix} \begin{pmatrix} \Delta x'' \\ \Delta y'' \\ \Delta z'' \end{pmatrix} \quad (2)$$

where;

Δx''=the desired incremental movement of the scope along the x'' axis of the third coordinate system.

Δy''=the desired incremental movement of the scope along the y'' axis of the third coordinate system.

Δz''=the desired incremental movement of the scope along the z'' axis of the third coordinate system.

a5 =the angle between the z' axis and the scope in the y'-z' plane.

a6 =the angle between the z' axis and the scope in the x'-z' plane.

Δx'=the computed incremental movement of the scope along the x' axis of the second coordinate system.

Δy'=the computed incremental movement of the scope along the y' axis of the second coordinate system.

Δz'=the computed incremental movement of the scope along the z' axis of the second coordinate system.

The angles a5 and a6 are provided by position sensors located on the end effector 32. The angles a5 and a6 are shown in FIG. 2.

The desired movement of the endoscope is converted from the second coordinate system to the first coordinate system by using the following transformation matrix;

$$\begin{pmatrix} \Delta x \\ \Delta y \\ \Delta z \end{pmatrix} = \begin{pmatrix} \cos(\pi) & -\sin(\pi) & 0 \\ \sin(\pi) & \cos(\pi) & 0 \\ 0 & 0 & 1 \end{pmatrix} \begin{pmatrix} \Delta x' \\ \Delta y' \\ \Delta z' \end{pmatrix} \quad (3)$$

where;

Δx'=the computed incremental movement of the scope along the x' axis of the second coordinate system.

Δy'=the computed incremental movement of the scope along the y' axis of the second coordinate system.

Δz'=the computed incremental movement of the scope along the z' axis of the second coordinate system.

π=is the angle between the first linkage arm and the x axis of the first coordinate system.

Δx=the computed incremental movement of the scope along the x axis of the first coordinate system.

Δy=the computed incremental movement of the scope along the y axis of the first coordinate system.

Δz=the computed incremental movement of the scope along the z axis of the first coordinate system.

The incremental movements Δx and Δy are inserted into the algorithms described above for computing the angular movements (Δa2 and Δa3 ) of the robotic arm assembly to determine the amount of rotation that is to be provided by each electric motor. The value Δz is used to determine the amount of linear movement provided by the linear actuator 24.

The surgical instrument is typically coupled to a camera and a viewing screen so that any spinning of the instrument about its own longitudinal axis will result in a corresponding rotation of the image on the viewing screen. Rotation of the instrument and viewing image may disorient the viewer. It is therefore desirable to maintain the orientation of the viewing image. In the preferred embodiment, the end effector has a worm gear (not shown) which rotates the surgical instrument about the longitudinal axis of the instrument. To insure proper orientation of the endoscope 16, the worm gear rotates the instrument 16 about its longitudinal axis an amount Δθ6 to insure that the y'' axis is oriented in the most vertical direction within the fixed coordinate system. Δθ6 is computed from the following cross-products.

$$\Delta\theta 6 = zi''x(yo''xyi'')$$

where;

Δθ6=the angle that the instrument is to be rotated about the z'' axis.

yo''=is the vector orientation of the y'' axis when the instrument is in the first position.

yi''=is the vector orientation of the y'' axis when the instrument is in the second position.

zi''=is the vector orientation of the z'' axis when the instrument is in the second position.

The vectors of the yi'' and zi'' axis are computed with the following algorithms.

$$[zi''] = \begin{bmatrix} \cos a6 & 0 & -\sin a6 \\ -\sin a5 \sin a6 & \cos a5 & -\sin a5 \cos a6 \\ \cos a5 \sin a6 & \sin a5 & \cos a5 \cos a6 \end{bmatrix} \begin{bmatrix} 0 \\ 0 \\ 1 \end{bmatrix}$$

$$xi'' = z \times zi''$$

-continued $$yi'' = zi'' \times xi''$$

where;
- a5=is the angle between the instrument and the z axis in the y-z plane.
- a6=is the angle between the instrument and the z axis in the x-z plane.
- z=is the unit vector of the z axis in the first coordinate system.

The angles a5 and a6 are provided by position sensors. The vector yo" is computed using the angles a5 and a6 of the instrument in the original or first position. For the computation of yi" the angles a5 and a6 of the second position are used in the transformation matrix. After each arm movement yo" is set to yi" and a new yi" vector and corresponding $\Delta\theta6$ angle are computed and used to re-orient the endoscope. Using the above described algorithms, the worm gear continuously rotates the instrument about its longitudinal axis to insure that the pivotal movement of the endoscope does not cause a corresponding rotation of the viewing image.

The system may have a memory feature to store desired instrument positions within the patient. The memory feature may be enabled either by voice commands or through a button on an input device such as the foot pedal. When a save command is spoken, the coordinates of the end effector in the first coordinate system are saved in a dedicated address(es) of the computer memory. When a return command is spoken, the processor retrieves the data stored in memory and moves the end effector to the coordinates of the effector when the save command was enabled.

The memory feature allows the operator to store the coordinates of the end effector in a first position, move the end effector to a second position and then return to the first position with a simple command. By way of example, the surgeon may take a wide eye view of the patient from a predetermined location and store the coordinates of that location in memory. Subsequently, the surgeon may manipulate the endoscope to enter cavities, etc. which provide a more narrow view. The surgeon can rapidly move back to the wide eye view by merely stating "AESOP return to one".

In operation, the user provides spoken words to the microphone. The phrase recognizer 86 matches the user's speech with stored words and provides matched electronic words to the processor 78. The processor performs a grammar process to determine whether the spoken words are robot commands. If the words are commands, the computer energizes the actuators and moves the endoscope, accordingly. The system also allows the user to control the movement of the endoscope with a foot pedal if voice commands are not desired.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A robotic system that controls a surgical instrument, comprising:
   a mechanism that can move the surgical instrument;
   an audio input device that receives a voice qualifier and a voice command from a user to move the surgical instrument, and provides an output signal that correspond to the voice command; and,
   a controller that receives said output signal from said audio input device and provides a movement output signal to said mechanism to move said mechanism and the surgical instrument in accordance with the voice command only when the voice qualifier accompanies the voice command.

2. The system as recited in claim 1, wherein said controller provides said movement output signal only when a plurality of voice commands are provided in a predetermined sequence.

3. The system as recited in claim 1, wherein said mechanism is a robotic arm assembly.

4. The system as recited in claim 1, further comprising a foot pedal coupled to said controller.

5. The system as recited in claim 1, further comprising a speaker coupled to said controller to generate an audio message.

6. The system as recited in claim 1, further comprising a monitor coupled to said controller to generate a visual message.

7. The system as recited in claim 1, wherein said controller provides said movement output signal only when a plurality of voice commands are provided in a predetermined sequence.

8. The system as recited in claim 1, wherein said mechanism is a robotic arm assembly.

9. The system as recited in claim 1, further comprising a foot pedal coupled to said controller.

10. The system as recited in claim 1, further comprising a speaker coupled to said controller to generate an audio message.

11. The system as recited in claim 1, further comprising a monitor coupled to said controller to generate a visual message.

12. A robotic system that controls a surgical instrument, comprising:
    a mechanism that can move the surgical instrument;
    audio input means for receiving a voice qualifier and a voice command from a user to move the surgical instrument and providing an output signal that correspond to the voice command; and,
    controller means for receiving said output signal from said audio input means and providing a movement output signal to said mechanism to move said mechanism and the surgical instrument in accordance with the voice command only when the voice qualifier accompanies the voice command.

13. The system as recited in claim 12, wherein said controller means provides said movement output signal only when a plurality of voice commands are provided in a predetermined sequence.

14. The system as recited in claim 12, wherein said mechanism is a robotic arm assembly.

15. The system as recited in claim 12, further comprising a foot pedal coupled to said controller means.

16. The system as recited in claim 12, further comprising speaker means for generating an audio message.

17. The system as recited in claim 12, further comprising monitor means for generating a visual message.

18. A method for moving a surgical instrument, comprising the steps of:
    a) generating a voice qualifier and a voice command to move a mechanism that holds the surgical instrument;
    b) determining whether the voice qualifier matches a first robot command;
    c) determining whether the voice command matches a second robot command if the voice qualifier matched the first robot command; and, d) moving the surgical instrument with said mechanism only if the voice qualifier matches the first robot command and the voice command matches the second robot command.

19. The method as recited in claim 18, wherein the surgical instrument is moved only when a plurality of voice commands are provided in a predetermined sequence.

20. A medical robotic system that controls a surgical instrument, comprising:

an actuator;

a linkage attached to said actuator and that can be coupled to the surgical instrument;

an audio input device that receives a voice qualifier and a voice command from a user; and, a controller that is coupled to said audio input device and provides a movement output signal to said actuator to move said linkage in accordance with the voice command only when the voice qualifier accompanies the voice command.

21. A robotic system that controls a surgical instrument, comprising:

a mechanism that can move the surgical instrument;

audio input means for receiving voice qualifier and a voice command from a user to move the surgical instrument; and, controller means for moving said mechanism in accordance with the voice command only when the voice qualifier accompanies the voice command.

22. The system as recited in claim 21, wherein said controller means provides said movement output signal only when a plurality of voice commands are provided in a predetermined sequence.

23. The system as recited in claim 21, wherein said mechanism is a robotic arm assembly.

24. The system as recited in claim 21, further comprising a foot pedal coupled to said controller means.

25. The system as recited in claim 21, further comprising speaker means for generating an audio message.

26. The system as recited in claim 21, further comprising monitor means for generating a visual message.

* * * * *